(12) United States Patent
Migeon et al.

(10) Patent No.: US 7,205,534 B2
(45) Date of Patent: Apr. 17, 2007

(54) METHOD AND APPARATUS FOR IN SITU DEPOSITING OF NEUTRAL CS UNDER ULTRA-HIGH VACUUM TO ANALYTICAL ENDS

(75) Inventors: Henri Noel Migeon, Tuntange (LU); Tom Wirtz, Grevenmacher (LU)

(73) Assignee: Centre de Recherche Public-Gabriel Lippmann, Belvaux (LU)

( * ) Notice: Subject to any disclaimer, the term of this patent is extended or adjusted under 35 U.S.C. 154(b) by 209 days.

(21) Appl. No.: 10/531,194

(22) PCT Filed: Oct. 24, 2003

(86) PCT No.: PCT/EP03/12074

§ 371 (c)(1),
(2), (4) Date: Apr. 13, 2005

(87) PCT Pub. No.: WO2004/038395

PCT Pub. Date: May 6, 2004

(65) Prior Publication Data
US 2006/0011865 A1    Jan. 19, 2006

Related U.S. Application Data

(60) Provisional application No. 60/421,203, filed on Oct. 25, 2002.

(51) Int. Cl.
*H01J 49/00*    (2006.01)
*H01J 37/305*    (2006.01)
(52) U.S. Cl. .................. 250/251; 250/309; 250/422.3; 250/288
(58) Field of Classification Search .............. None
See application file for complete search history.

(56) References Cited

U.S. PATENT DOCUMENTS 2,972,115 A  *  2/1961  Zacharias et al. .............. 331/3

FOREIGN PATENT DOCUMENTS

GB    1 315 647    5/1973

OTHER PUBLICATIONS

T. Wirtz et al. "Useful Yields of MCs$^+$ and MCs$_2$$^x$ clusters: a comparative study between the Cameca IMS 4f and the Cation Mass Spectometer" International Journal of Mass Spectrometry 209 (2001) p. 57-67.
Th. Mootz et al."Cation Mass Spectrometer: an Instrument Dedicated to the Analysis of MCs$_x$$^+$ Clusters. Description of the Instrument and Preliminary Results" Proceedings of the 12th International Conference on Secondary Ion Mass Spectrometry, Brussels, Belgium Sep. 5-11 1999 p. 233-236.
M. Kamaratos. "Adsorption kinetics of Cs-O activation layer on GaAs (1 0 0)" Applied Surface Science 185 (2001) p. 66-71.

* cited by examiner

*Primary Examiner*—Nikita Wells
(74) *Attorney, Agent, or Firm*—Merchant & Gould P.C.

(57) ABSTRACT

The present invention relates to a method for modifying the electronic properties of a surface to analytical ends, such as SIMS or electron spectroscopy, characterised in that it comprises in situ deposition of pure neutral cesium (Cs$^0$), under ultra-high vacuum, said neutral cesium being enabled in the form of a collimated adjustable stream. The invention relates also to the special column designed for implementing the method and to the corresponding energy and/or mass analyser instrument.

17 Claims, 10 Drawing Sheets

METHOD AND APPARATUS FOR IN SITU DEPOSITING OF NEUTRAL CS UNDER ULTRA-HIGH VACUUM TO ANALYTICAL ENDS

FIELD OF THE INVENTION

The present invention relates to a new Secondary Ion Mass Spectroscopy (SIMS) method operating in the $MCs_x^+$ (x=1,2) mode. The method has been carried out in a Cation Mass Spectrometer (CMS) developed and modified by the inventors for reaching high secondary emission useful yields combined with excellent depth and lateral resolution.

The invention also relates to the modified CMS, in particular by means of a cesium deposition column which is coupled with traditional primary bombardment column.

PRIOR ART AND RELATED TECHNICAL BACKGROUND

Owing in particular to its excellent sensitivity and its good depth resolution, Secondary Ion Mass Spectrometry (SIMS) constitutes an extremely powerful technique for analysis of surfaces and thin films. Its main fields of application lie in the semiconductor, glass, organic and metallurgical composite materials.

SIMS instruments also allow the recording of ion images of the surface of the analysed sample. In this case, a thin ion probe sweeps the surfaces of the sample and the secondary ions which have suitably selected mass are recorded with respect to the position on the surface from which they originate. An emerging field of application for this imaging technique providing good lateral resolution combined with excellent sensitivity is situated in particular in biology.

Alongside all its advantages, however, the SIMS technique suffers from one major drawback: the measurements can only be quantified with difficulty. The intensity of the measured signals is generally greatly dependent on the sample analysed, given that the ionisation yield of a given sputtered element may vary by several orders of magnitude depending on the composition of the matrix in which it is located. This phenomenon is known as the matrix effect.

In order to get round these problems linked to the matrix effect, the SIMS analyses are increasingly carried out in $MCs_x^+$ mode. This method consists in incorporating cesium (Cs) in the material of interest and detecting positive ion clusters formed by the recombination of an atom of the element M in which one is interested together with one or two atoms of Cs. Given that these $MCs_x^+$ clusters are formed by atomic recombinations above the surface of the sample, the composition of the matrix does not come any longer into play directly, consequently eliminating the matrix effect.

SIMS instruments of prior art have exclusively used a beam made of $Cs^+$ primary ions in order to perform analyses in the $MCs_x^+$ mode. A number of drawbacks are still to be listed with this respect.

Optimisation of the Cs Concentration to form $MCs_x^+$ Clusters

When the analyses in $MCs_x^+$ mode are carried out by bombarding the sample with a beam of $Cs^+$ ions, this beam serves both for the incorporation of Cs in the material and for the sputtering of the surface. In this case, the Cs concentration, which is a crucial parameter determining the sensitivity of the analysis, as shown in FIG. 1, is set by the primary bombardment conditions—mainly the angle and energy of impact—which can be adapted only in a very limited way on conventional SIMS equipment. Consequently, the Cs concentration is practically fixed for a given type of sample and cannot be chosen freely. As it is unlikely that the Cs concentration thus obtained will coincide with the optimum concentration for the material in question, the analysis is not optimised.

Coupling of the Cs Concentration and the Depth Resolution

A second major disadvantage of the use of $Cs^+$ ion bombardment relates to the impossibility of separately choosing the Cs concentration ($c_{Cs}$) implanted in the sample and the energetic and angular parameters of the primary beam, given that the latter determine the value of $c_{Cs}$. Now the primary bombardment conditions also considerably affect major analytical characteristics such as the depth resolution.

Pre-Equilibrium State

The introduction of Cs into the material by ion bombardment does not allow an optimum Cs concentration to be attained right from the first atomic layer, given that the Cs atoms are implanted under the surface, as shown in FIG. 2, at greater or lesser depth depending on their impact energy. Consequently, the analysis is inconclusive in the pre-equilibrium state which precedes the achieving of a constant concentration of Cs (in a $Cs^+$ bombardment) or Cs and Ga (in a $Cs^+$ and $Ga^+$ bombardment).

Optimisation of Formation of Negative Secondary Ions

Furthermore, bombardments by electropositive elements are often used to raise the negative ion yield by several orders of magnitude. In this context, the emission of negative secondary ions is greatly enhanced by the presence of Cs atoms on the surface of the sample which is bombarded.

Aims of the Invention

The present invention aims at providing a new Secondary Ion Mass Spectroscopy (SIMS) method operating in the $MCs_x^+$ (x=1,2) mode permitting to separately choose the Cs concentration implanted in the sample and the sputtering of the sample surface, leading thus to simultaneous optimisation of the Cs concentration and analytical parameters, such as depth resolution, which depend now exclusively on primary bombardment conditions.

Particularly, the invention aims at permitting one, by depositing neutral Cs atoms on the sample surface, to vary the Cs concentration continuously in the range quasi 0 to 100% to an optimum value in order to maximise detected $MCs_x^+$ and $Cs_x^+$ signals for any kind of sample.

Additionally, the invention aims at enabling an optimised signal to be measured right from the first atomic layer.

Another goal of the present invention is to provide a specially-developed cesium column with significant service life increase and designed to considerably reduce the risk of contaminating of the cesium deposit as well as of the analysis chamber with traces of other elements.

SUMMARY OF THE INVENTION

A first object of the present invention relates to a method for modifying the electronic properties of a surface to analytical ends, characterised in that it comprises in situ deposition of neutral cesium ($Cs^0$), under ultra-high vacuum (residual pression of about $10^{-9}$–$10^{-10}$ mbar), said neutral cesium being enabled in the form of a collimated adjustable stream.

According to the invention, the stream of $Cs^0$ is provided and collimated in a column by means of:

a temperature adjustment of an evaporator comprising a metallic cesium reservoir, and/or an aperture control of a motorised obturator located in the path of the cesium stream.

It was particularly contemplated by the inventors that said $Cs^0$ deposition be simultaneously accompanied by a primary bombardment comprising electrons and/or ions or neutral atoms or groups of atoms, or by an X-ray irradiation, intended to induce an emission of a beam of particles for analysis, out of the surface.

Preferably, the method of the invention is coupled to static or dynamic Secondary Ion Mass Spectroscopy (SIMS), preferably operating in the $MCs_x^+$ mode (x=1, 2).

Advantageously, the deposition rate of $Cs^0$ is continuously adjustable in the range from 0 to 10 Å/s, corresponding about to 0–4 monolayers per second.

According to another preferred embodiment, the method of the invention is coupled to electron spectroscopy, preferably Auger Electron Spectroscopy (AES), Electron Energy Loss Spectroscopy (EELS), X-Ray Photoemission Spectroscopy (XPS) or Ultraviolet Photoemission Spectroscopy (UPS).

According to the SIMS embodiment, the secondary beam for analysis comprises secondary electrons and/or $Cs_x^{n+}$ and/or $MCs_x^{n+}$ positive clusters and/or $M^{m-}$ negative ions and/or $M^{m+}$ positive ions, M being a constituent of the sample material made of an atom or a group of atoms (n, m integers).

Advantageously, the sputtering and Cs introduction phases are decoupled during analyses in the $MCs_x^+$ mode, in a simultaneous optimisation of deposited Cs concentration and analytical characteristics, such as the depth resolution.

Still more advantageously, the depth resolution solely depends on the bombardment conditions for the analysis.

The method of the invention further enables a stream of a chemical element other than Cs, evaporated under ultra-high vacuum, to create secondary emission for analytical purposes of $M_1M_2^{n+}$ clusters or $M_2^{m-}$ ions or $M_2^{m+}$ ions (n, m integers) or electrons, wherein $M_1$ and $M_2$ are respectively the atoms or groups of atoms constituted by the chemical element other than Cs and the atoms or groups of atoms from the sample.

Still advantageous, the sole adjustable deposition rate of $Cs^0$ or a chemical element other than Cs to an optimised value enables to optimise the intensity of the secondary particles emitted by the sample.

According to a preferred embodiment, the reservoir temperature range is maintained between 70 and 90° C., corresponding to a pressure range from $1.10^{-4}$ to $4.10^{-4}$ mbar and in that the stability of the deposition rate is about 2% over 60 minutes.

Under bombardment analysis mode, the deposited $Cs^0$ concentration is solely related to the respective Cs and sample densities ($\rho_{Cs}$, $\rho_M$), to the sputtering yield in the given bombardment conditions (Y) and to the ratio between the $Cs^0$ erosion ($V_{er}$) and the deposition ($V_D$) rate ($\tau=V_{er}/V_D$)

A significant advantage of the invention resides in the fact that the useful yield, i.e. the sensitivity, of the secondary emission species, preferably $M^{n-}$, $M^{m+}$, and still more preferably $Cs_x^{n+}$ and $MCs_x^{n+}$, is approximately solely related to said ratio ($\tau$) and not to the respective erosion and deposition rate taken individually and in that the secondary signal is optimisable by adjusting the $Cs^0$ deposition rate to attain an optimum value of said ratio ($\tau$).

Preferably, the stream of $Cs_0$ is automatically and continuously adapted via the obturator.

A second object of the invention relates to an energy and/or mass analyser instrument, for carrying out the method described, comprising a neutral cesium ($Cs^0$) deposition column capable of delivering an adjustable and stable stream of pure neutral cesium, said column being preferably usable simultaneously with a primary bombardment or a primary irradiation column.

The instrument preferably is a static or dynamic secondary ion mass spectrometry (SIMS) instrument, comprising a primary bombardment column and a secondary column equipped with secondary ion extraction means, a mass spectrometer, preferably of the type TOF (Time-Of-Flight), quadrupolar or with magnetic sector and ion detection means.

A third object of the invention relates to a neutral cesium column usable in an instrument, such as described. The neutral cesium column comprises an evaporation block including a reservoir filled with pure metallic cesium, equipped with temperature control means, prolonged by a tube up to a gun end piece located close to the sample and equipped with beam collimation means.

Advantageously, said beam collimation means comprise a motorised continuously adjustable obturator, preferably comprising a rotary disk using a slit of continuously variable width, said disk being driven by a stepper motor.

Still advantageously, at the operation temperature, the neutral cesium ($Cs^0$) is in liquid state and the evaporation block lies with an inclination angle such as said liquid remains in the bottom of the reservoir under gravity effect.

Still advantageously, said tube and gun end piece equipped with beam collimation means are further equipped with temperature control means for preventing condensation and obturation risks.

Preferably, the evaporator bloc is located in an external part which can be isolated from the main chamber of the instrument by means of a gate valve and capable of being separately pumped and vented.

SHORT DESCRIPTION OF THE DRAWINGS

Figure 1:
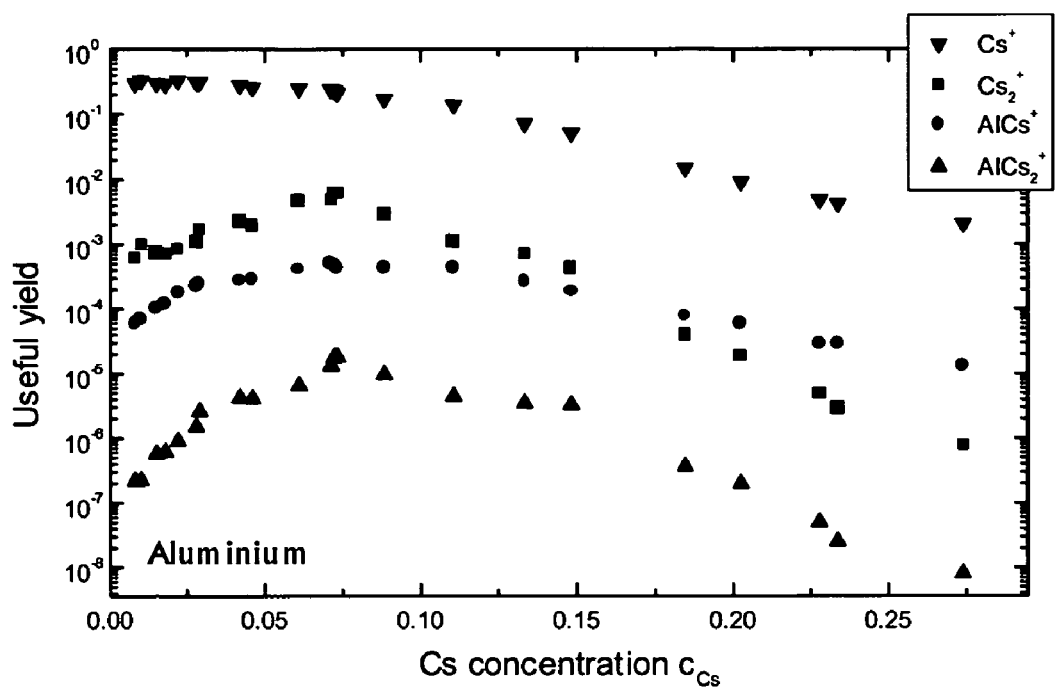
FIG. 1 represents the evolution of useful yields (i.e. sensitivity) as a function of the Cs concentration for the aluminium sample ($Cs^+$ or $Cs^+/Ga^+$ primary ion bombardment).
Figure 2:
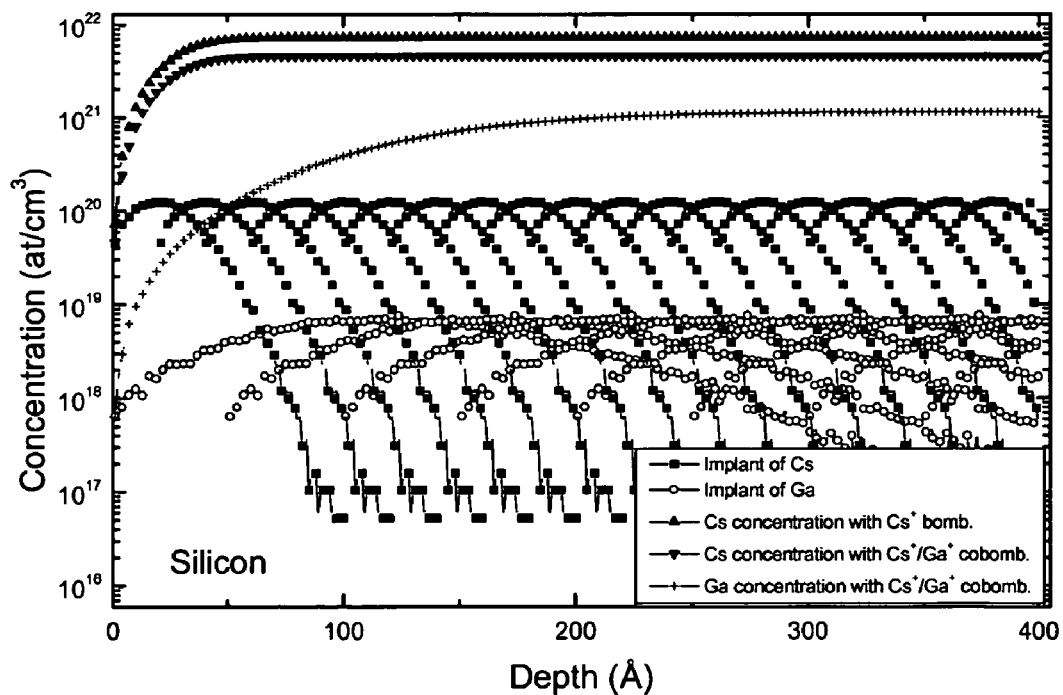
FIG. 2 represents the depth evolution of Cs concentration implanted in a silicon sample for two different modes of analysis : pure $Cs^+$ bombardment and $Cs^+/Ga^+$ co-bombardment.
Figure 4:
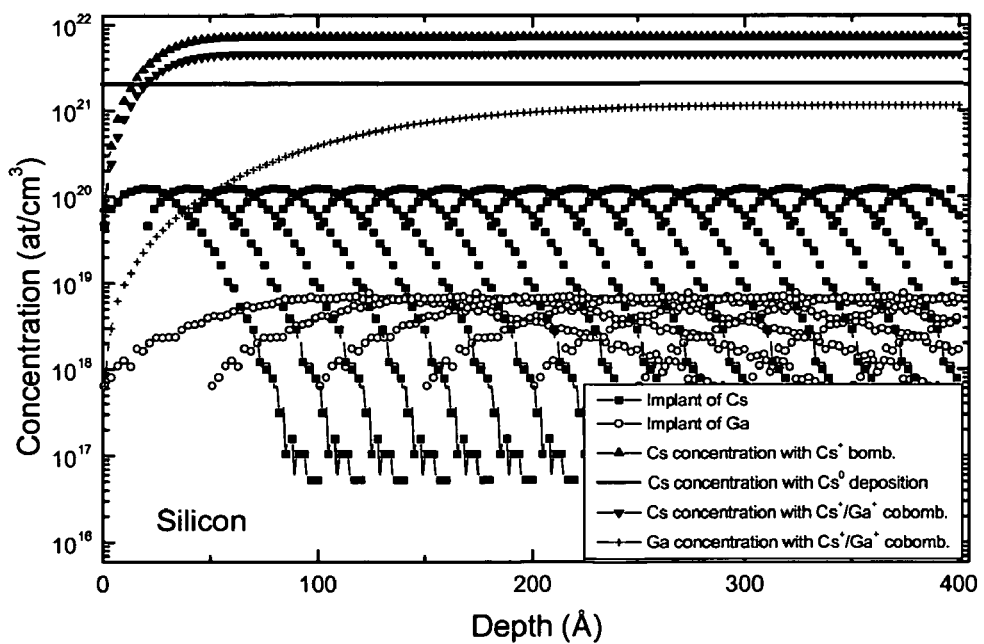

FIG. 4 comparatively represents the depth evolution of the Cs concentration in silicon for three different modes of analysis : pure $Cs^+$ bombardment, $Cs^+/Ga^+$ co-bombardment and $Ga^+$ bombardment with $Cs^0$ deposition, the latter corresponding to the difference with FIG. 2.

Figure 5:
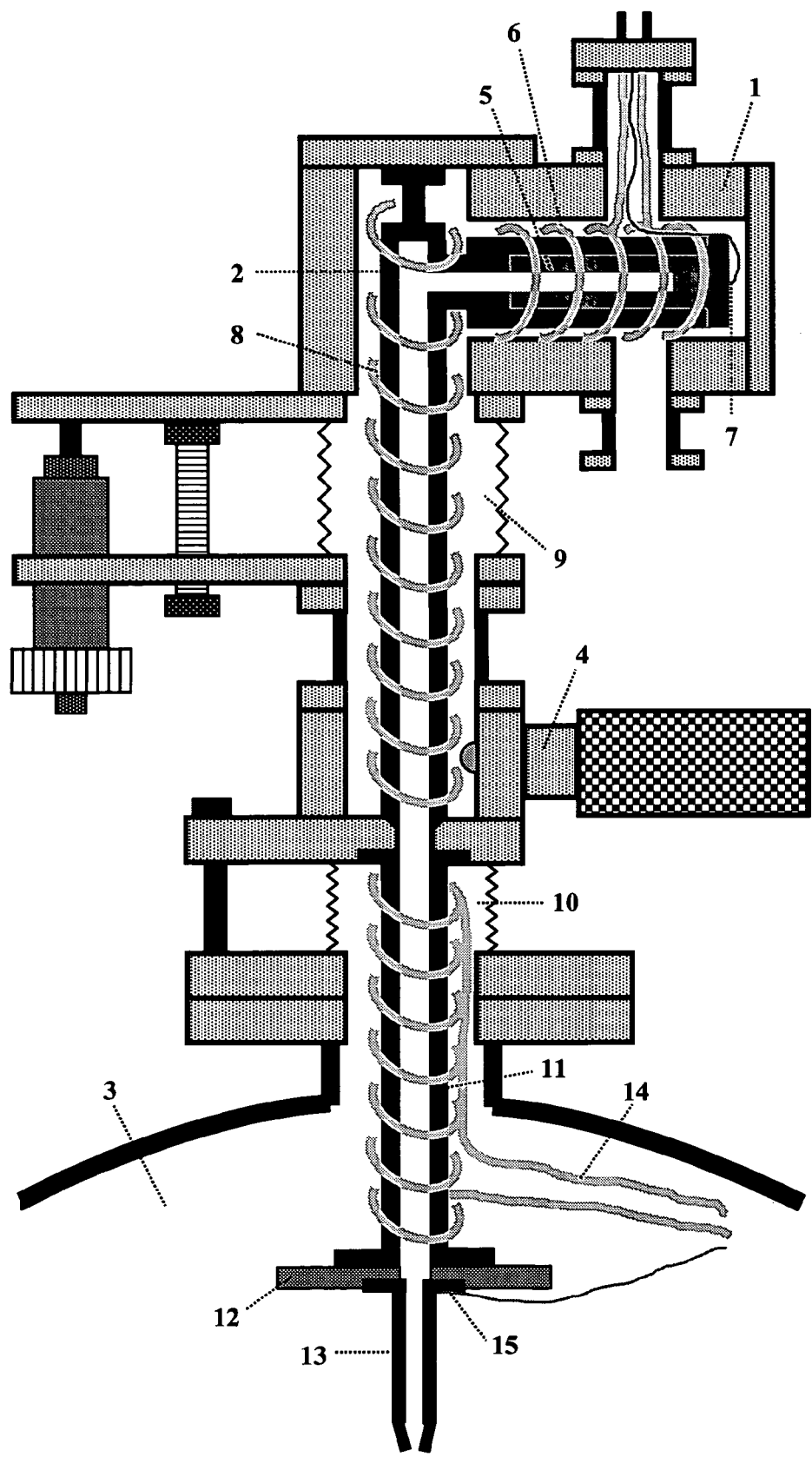

FIG. 5 represents a schematic overall view of the $Cs^0$ evaporator of the invention, wherein the external and internal parts are separated at the gate valve.

Figure 6:
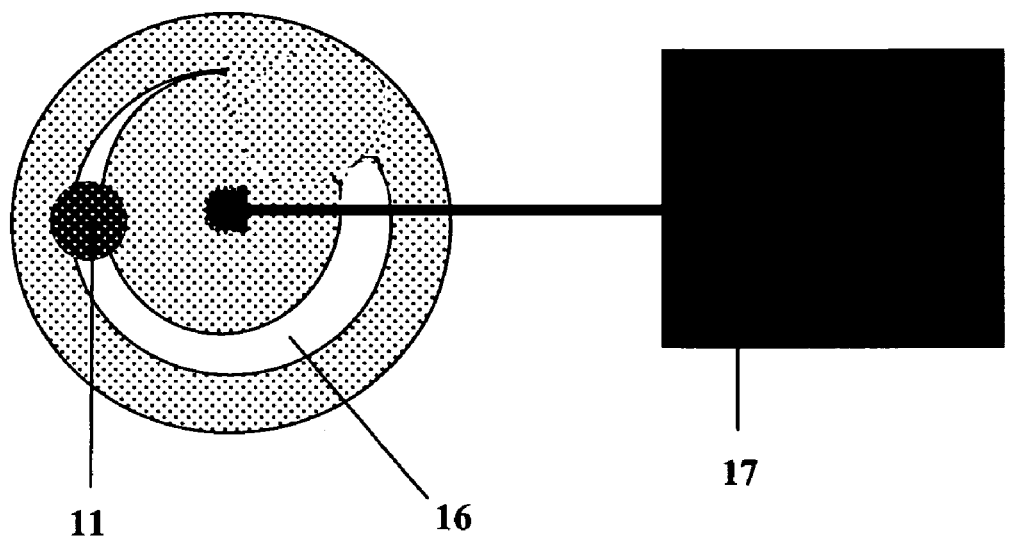

FIG. 6 represent a schematic representation of a preferred obturator embodiment.

Figure 7:
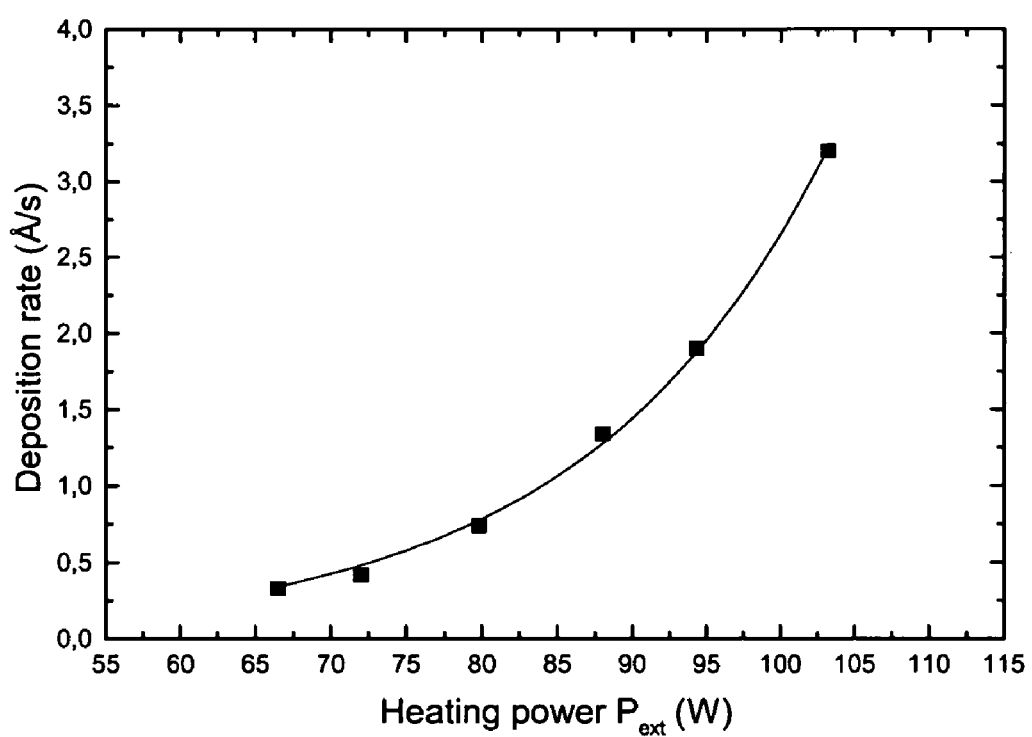

FIG. 7 represents the change in the $Cs^0$ deposition rate on the sample as a function of the heating power transmitted to the neutral cesium reservoir.

Figure 8:
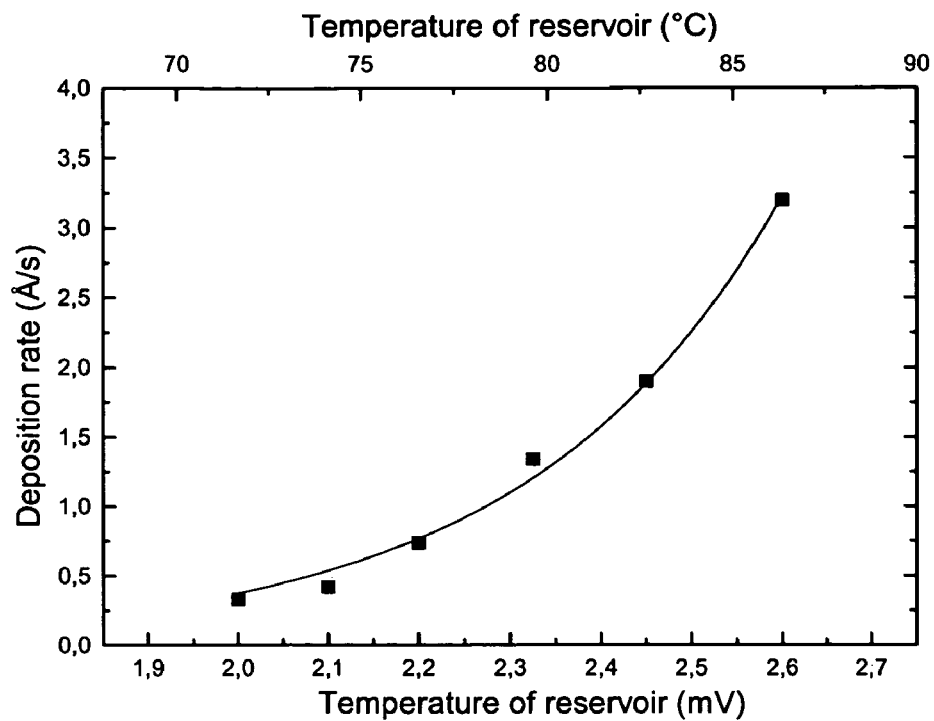

FIG. 8 represents the change in the $Cs^0$ deposition rate onto the sample as a function of the temperature (in mV) of said reservoir.

Figure 9:
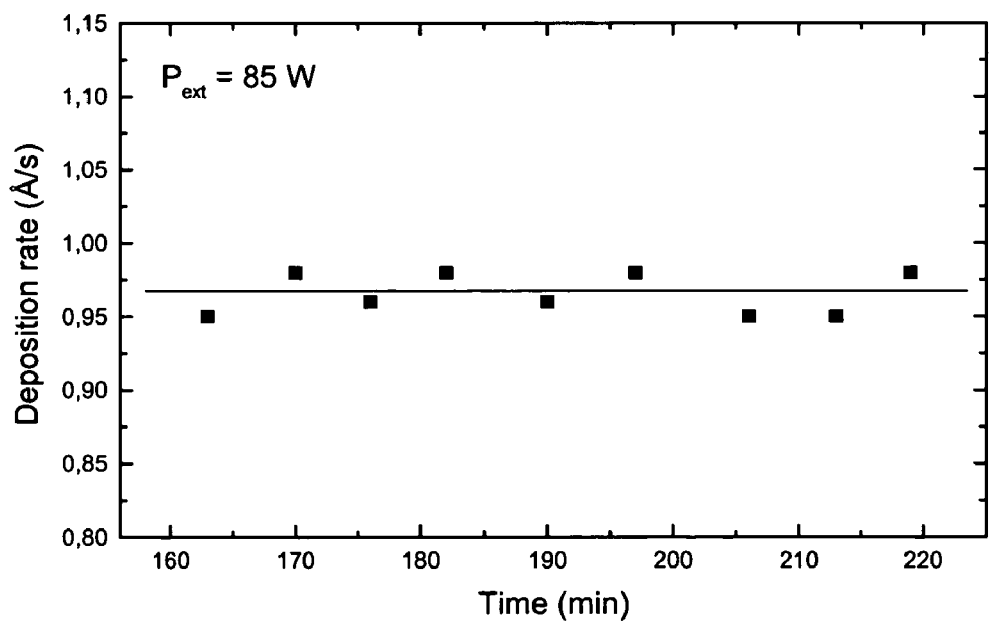

FIG. 9 represents the fluctuation of the $Cs^0$ deposition rate indicated by the quartz microbalance controller over a one-hour period for a reservoir heating power of 85 W. The solid line indicates the average value.

Figure 10:
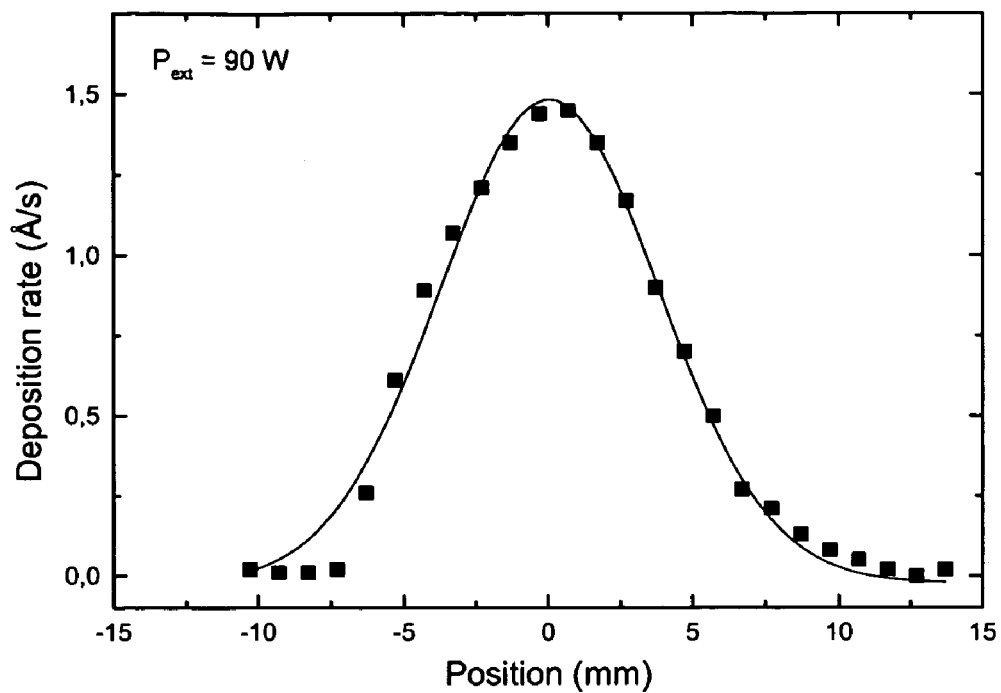

FIG. 10 represents the profile of the $Cs^0$ beam recorded by determining the deposition rate for different positions of the quartz balance. The abscissa 0 corresponds to the position located directly below the secondary ion extraction nose. The continuous curve approximates the experimental points by a Gaussian.

Figure 11:
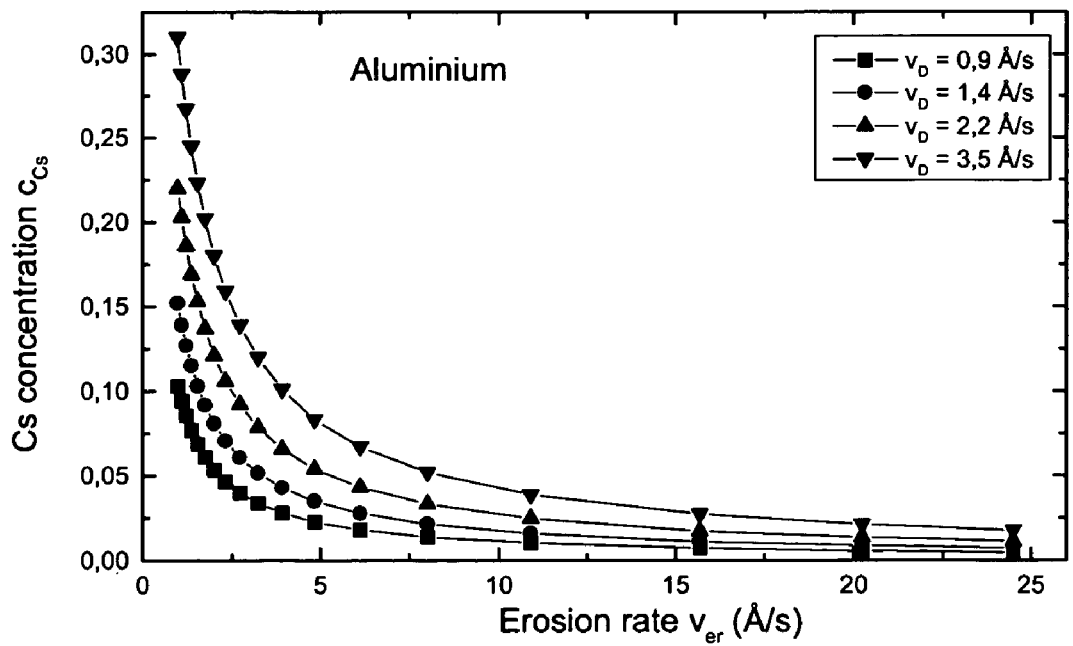

FIG. 11 represents the variation of the Cs concentration determined experimentally for four different $Cs^0$ deposition rates with respect to different erosion rates for an aluminium sample.

Figure 12:
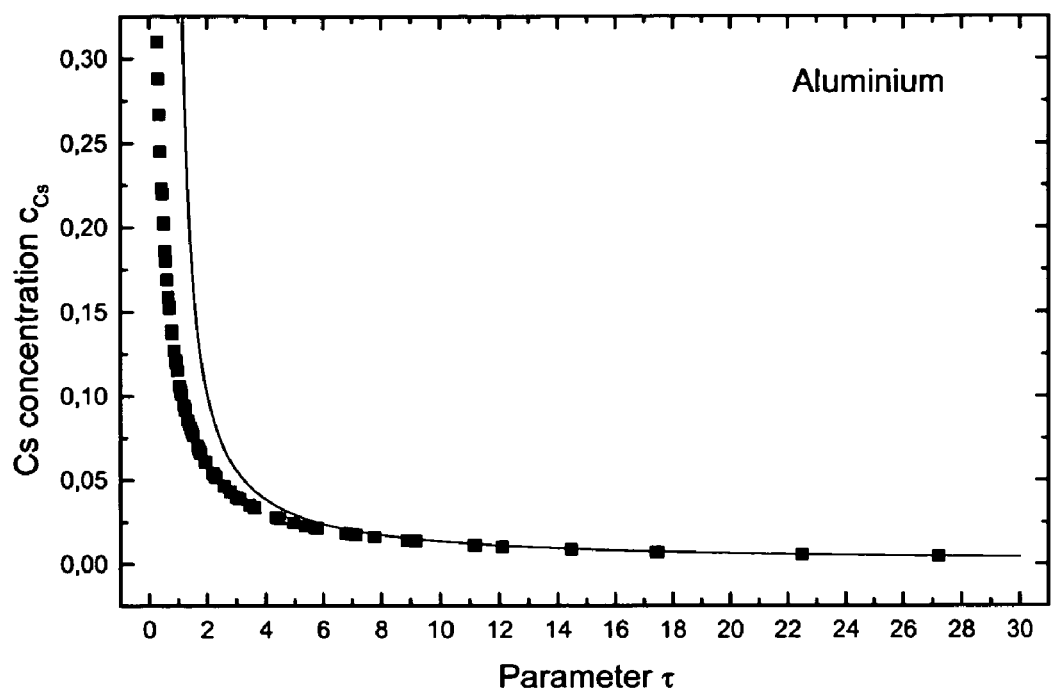

FIG. 12 represents the experimental change (squares) and theoretical change (solid curve) of the Cs concentration as a function of the parameter $\tau$ for the aluminium sample.

Figure 13:
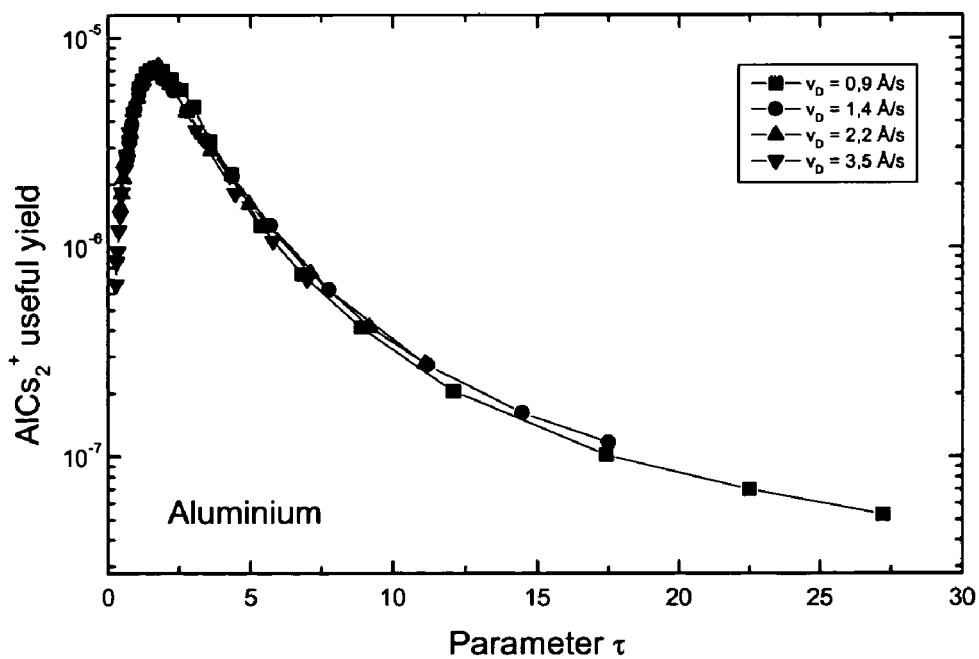

FIG. 13 represents the change in the useful yield of the sputtered $AlCs_2^+$ cluster of a sample of aluminium as a function of the characteristic parameter $\tau$.

Figure 14:
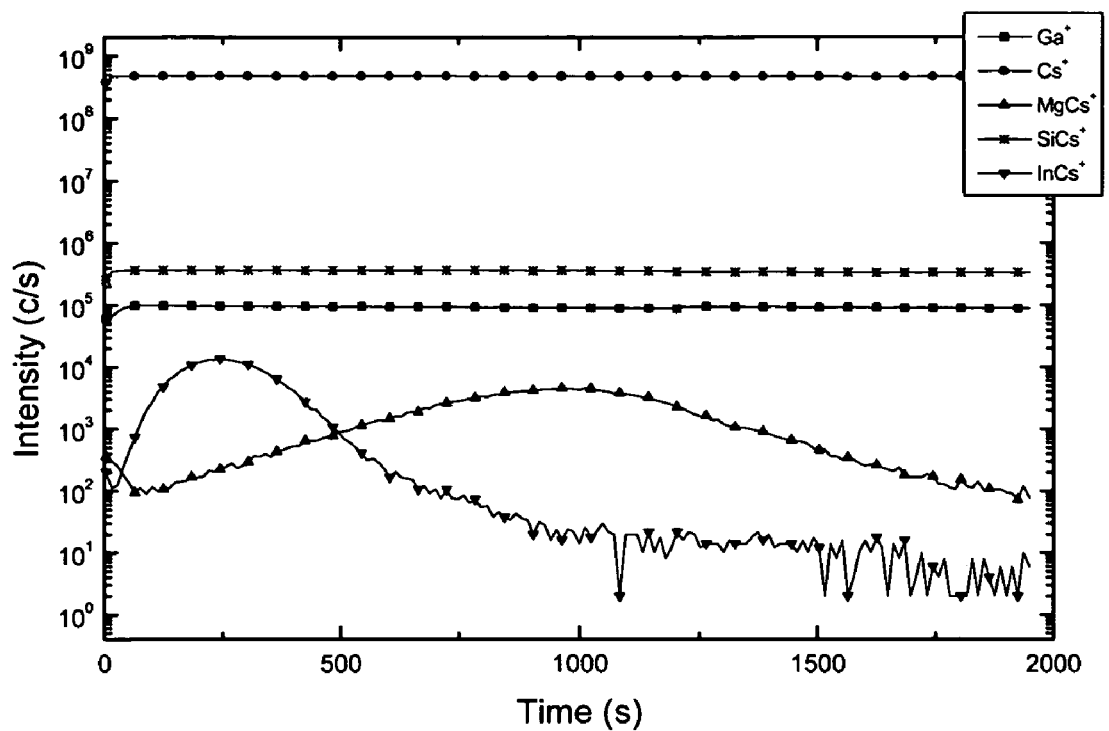

FIG. 14 represents the SIMS depth profile of a sample of Si subjected to an implantation of Mg and In.

Figure 15:
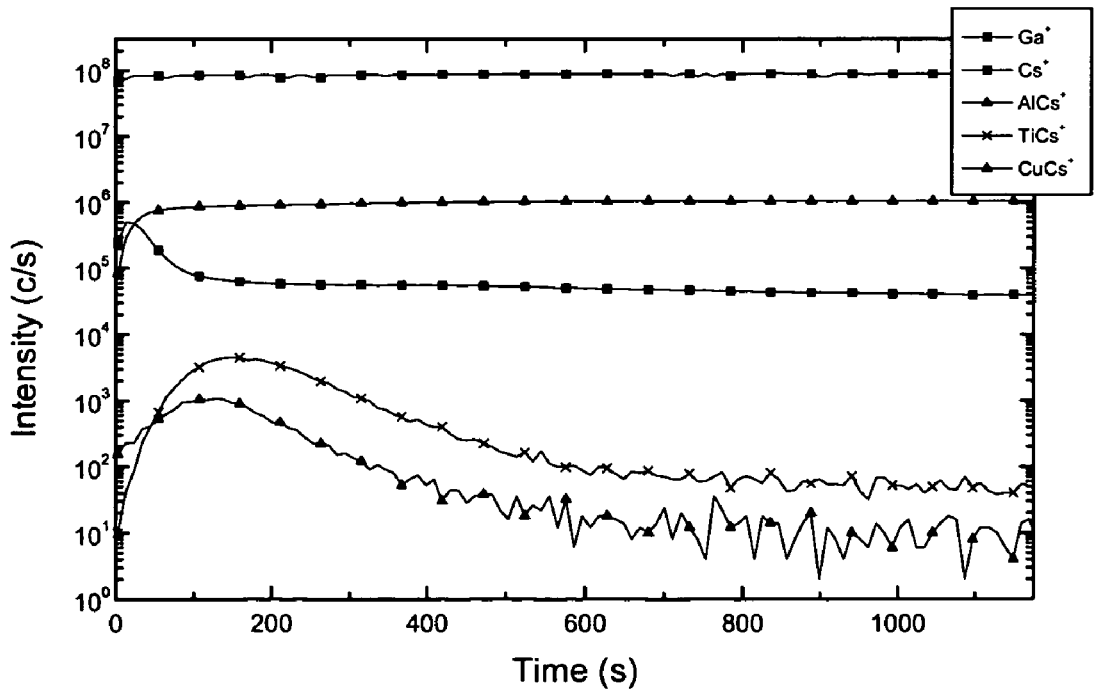

FIG. 15 represents the SIMS depth profile of a Al sample subjected to an implantation of Ti and Cu.

Figure 16:
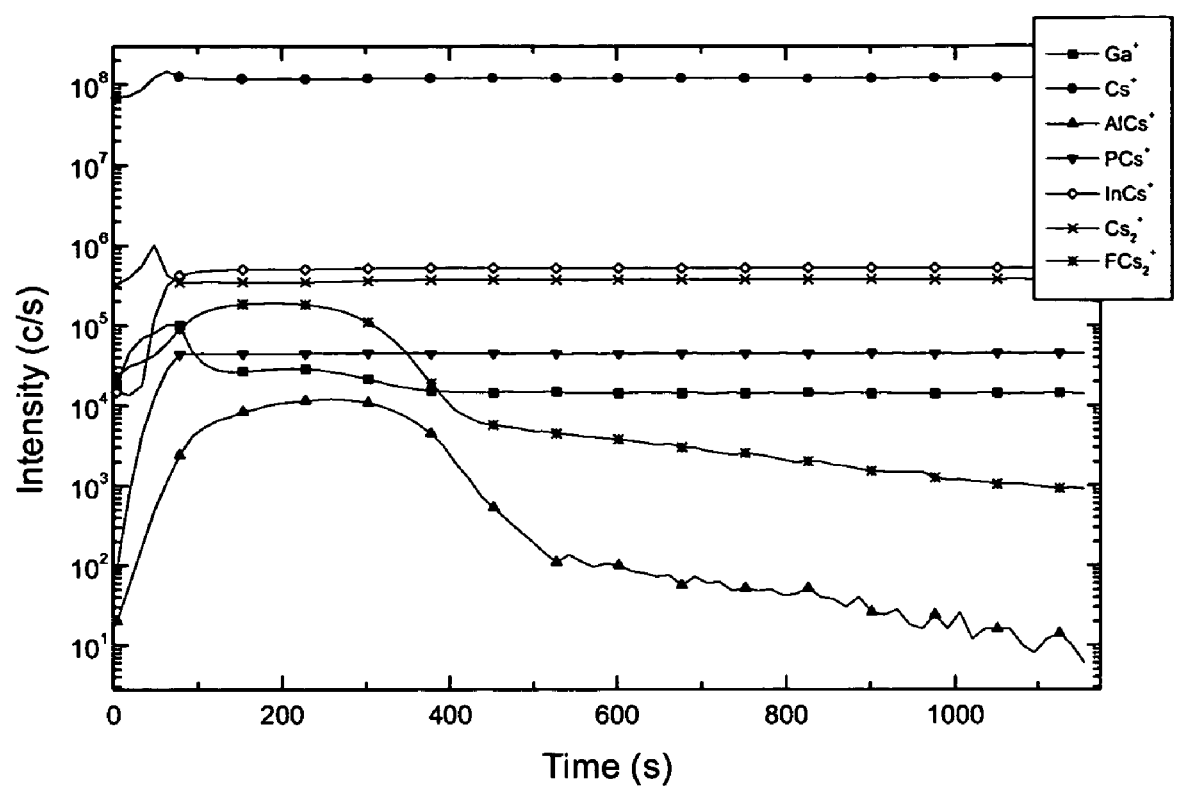

FIG. 16 represents the SIMS depth profile of a sample of InP subjected to an implantation of F and Al.

Figure 17:
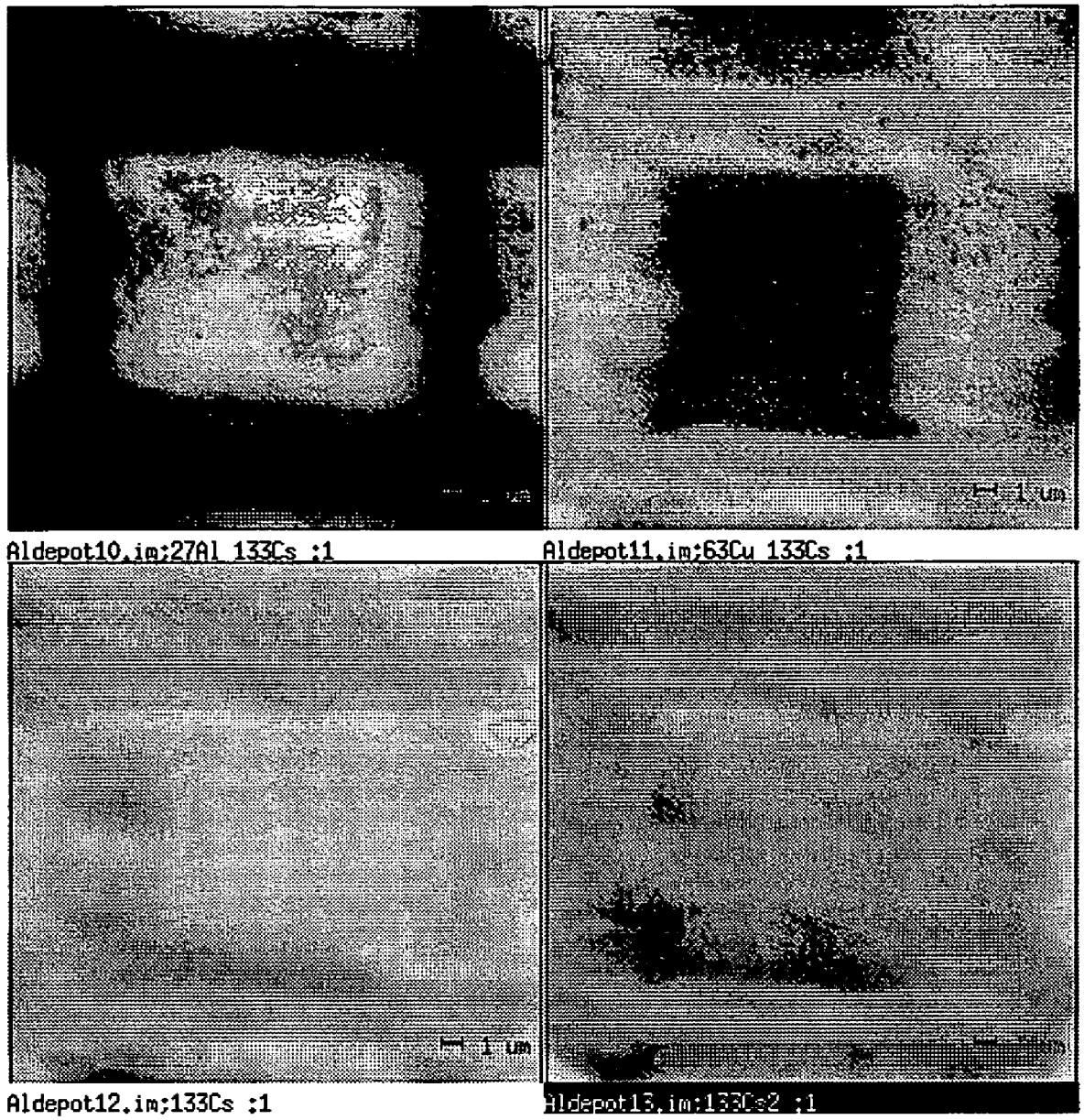

FIG. 17 respectively represents $AlCs^+$, $CuCs^+$, $Cs^+$ and $Cs_2^+$ secondary ion images of the same area of an Al/Cu grid.

DESCRIPTION AND ADVANTAGES OF THE INVENTION

The Laboratory for the Analysis of Materials (LAM) of the Centre de Recherche Public—Gabriel Lippmann has developed and installed on the Cation Mass Spectrometer (CMS), which is a prototype scientific instrument [1,2], a column which allows an adjustable and collimated stream of neutral cesium ($Cs^0$) to be deposited on the surface of the material sample to be analysed.

Using this new column, it was possible to introduce an analysis technique consisting of a $x^{y+}$ ion bombardment accompanied by a deposit of $Cs^0$ at the surface of the sample. This experimental technique permits to avoid the constraints imposed by a $Cs^+$ ion bombardment which were described above in the prior art section.

Figure 3:
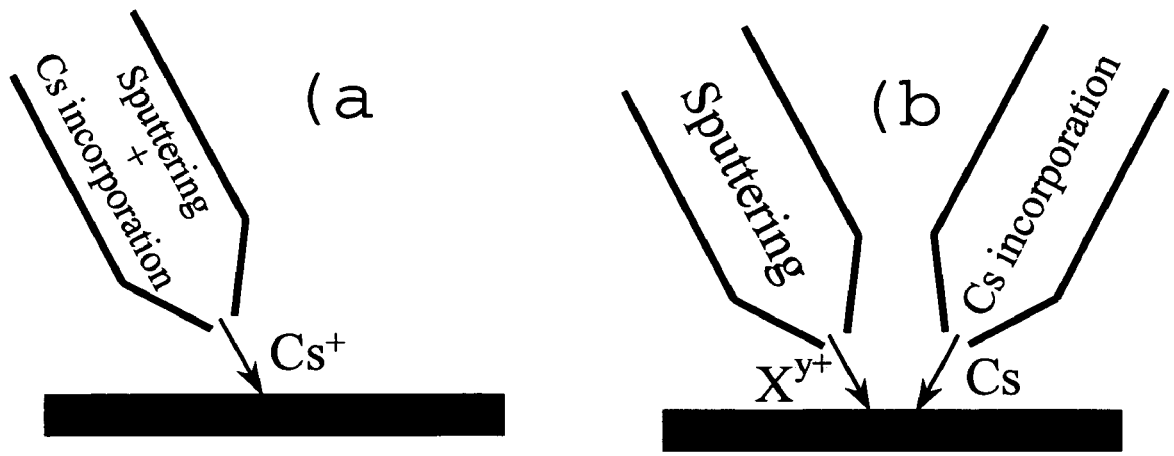
FIG. 3 represents the principle of analyses grouping together the sputtering and Cs incorporation stages (a) and those separating these two stages (b).

This new analysis technique provides an additional degree of freedom by separating the sputtering and Cs introduction phases of analyses in $MCs_x^+$ mode with aiming at a simultaneous optimisation of the Cs concentration and of the major analytic characteristics such as the depth resolution which mainly depend on the primary bombardment conditions. The principle of the invention is roughly illustrated in FIG. 3.

When the optimum quantity of Cs is deposited in the form of neutral atoms on the surface of the sample, no sputtering process or atomic mixing of the target takes place and the depth resolution of the analysis depends, advantageously, solely on the characteristic conditions of the bombardment produced by the sputtering/analysis gun.

On the other hand, the use of the Cs evaporator which deposits the Cs atoms right from the surface of the sample enables an equilibrium state to be attained from the first atomic layer, as shown in FIG. 4. This new analysis technique therefore offers a considerable advantage in the analysis of samples in which the interesting zone is in the close vicinity of the surface.

Finally, this same $Cs^0$ column also enables optimisation of the negative secondary ions by depositing the optimum quantity of Cs.

REFERENCES

[1] T. Mootz, B. Rasser, P. Sudraud, E. Niehuis, T. Wirtz, W. Bieck, H. -N. Migeon, in A. Benninghoven, P. Bertrand, H. -N. Migeon, H. W. Werner (Eds.), Secondary Ion Mass Spectrometry SIMS XII, Elsevier, Amsterdam, 2000, p. 233–236.

[2] T. Wirtz, B. Duez, H. -N. Migeon, H. Scherrer, Int. J. Mass Spectrom. 209 (2001) 57.

DESCRIPTION OF A PREFERRED EMBODIMENT OF THE INVENTION

1. The $Cs^0$ Evaporator 1.1. Operating Principle

To deposit alkaline metals, laboratories almost exclusively use getters, marketed by the Italian group SAES, containing the alkaline metal X in the form of chromate $X_2CrO_4$ and a $Zr_xAl_y$ type powder acting as a reducing agent 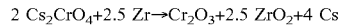 in order to release the X (i.e. Cs) atoms. When this mixture is heated by circulating an electric current, the reduction reaction is activated and the quantity of alkaline atoms thus produced depends on the heating power. In the case of Cs, this reduction reaction is written as follows:

2 $Cs_2CrO_4$+2.5 Zr→$Cr_2O_3$+2.5 $ZrO_2$+4 Cs

The use of such a getter on the CMS machine to carry out the optimisations cited here above nevertheless presents several major drawbacks. First of all, preliminary calculations have shown that, in standard bombardment conditions, a Cs deposition rate of approximately 1 Å/s would be appropriate. To attain such a stream of Cs atoms on the surface of the sample while at the same time choosing an acceptable source-sample distance, it is necessary for the getter to emit at a rate of approximately $4.10^{14}$ atomes/s, which corresponds to $8.8.10^{-8}$ g/s. Now as a 1 cm-long getter is filled with 4.4 mg of Cs and such a length may not be exceeded in order to guarantee that the majority of the Cs atoms are deposited in the zone to be analysed, the Cs source would have a service life of only $5.10^4$ s or 14 hours. As the stream of Cs atoms is not collimated and therefore covers a much bigger space than necessary, the service life calculated in this way represents a theoretical upper limit.

The impossibility of directing the Cs stream exclusively onto the analysis zone is a second major disadvantage of getters. In addition to the considerable loss of useful Cs atoms, such an uncollimated emission is also very likely to contaminate the whole analysis chamber by depositing a conductive and highly reactive film on all the surfaces, including ceramics serving as electrical insulators which will thereby be rendered ineffective.

Finally, the vapours emitted by commercial getters always contain traces of other elements originating mainly in the reducing agents used. This contamination of the Cs deposit is likely to increase the detection limits for certain elements given that the signal of the element in question would be affected by a background noise of varying degrees of intensity.

In view of these service life drawbacks, contamination of the analysis chamber and cleanliness of the Cs deposit, we decided not to use a conventional getter to equip the CMS machine of the invention.

As an alternative, we developed a source emitting a stream of Cs from the evaporation of pure metallic Cs. This configuration was intended to enable the elimination of at least the first two major disadvantages of conventional getters mentioned above. Indeed, the service life can be increased enormously (by a factor of 1000) given that it is possible to fill the reservoir with a large quantity of Cs (several grams) and given that the Cs beam can be collimated on the useful zone by using a gun end piece with a small opening positioned close to the sample. Finally, as the evaporator is loaded with pure metallic Cs, the risk of contaminating the Cs deposit with traces of other elements is also reduced.

1.2. Description

The Cs evaporator specially designed for the CMS machine of the invention comprises two separate parts, as shown in FIG. 5. While the first part is located completely inside the main chamber of the CMS instrument, the second part is mounted outside the chamber using a 40CF flange. Because of their respective positions with respect to the main chamber, the two parts will henceforth be referred to as the "internal" and "external" parts.

1.2.1. External Part

The external part of the evaporator comprises an actual evaporation block 1 and a tube (primary tube 2) guiding the stream of gaseous Cs towards the internal part of the evaporator. It can be isolated from the main chamber 3 of the CMS machine by means of a gate valve 4 and be independently pumped or vented.

The evaporation block 1 is a solid cast stainless steel part. This block contains a cylindrical housing in which the reservoir 5 containing the metallic Cs slides. The maximum capacity of this reservoir is 7.6 g of Cs. To prevent the liquid Cs from flowing out into the whole volume of the evaporator, the evaporation block is mounted on the external part of the evaporator with an angle of inclination such that all the liquid Cs remains at the bottom of the reservoir under the effect of gravity. To obtain gaseous Cs, the housing of the reservoir is wound round with a "Thermocoax"-type heating wire 6 capable of supplying the thermal energy necessary for the evaporation of the Cs. The temperature of the reservoir is measured by means of a chromel-alumel thermocouple 7 screwed to the end of the reservoir.

At the evaporation block exit, the Cs vapour escapes through an 8 mm hole in a stainless steel tube which also has a diameter of 8 mm and a length of 180 mm, which guides the gas towards the entry of the internal part of the evaporator. To avoid condensation of the Cs on the walls of this guide tube, the tube is wound round with a heating wire 8 lodged in grooves.

The external and internal parts are separated by a gate valve 4 enabling the evaporation block to be isolated from the main chamber 3 when the evaporator 5 is not in operation. When the evaporator is in operation, the two parts are brought back into contact with each other by moving the external part by means of a bellows-operated translator 9.

1.2.2. Internal Part

The internal part of the evaporator serves to deliver the stream of neutral Cs onto the zone to be analysed in the form of a jet of sufficiently reduced diameter to avoid any contamination of the analysis chamber 3. The whole of the internal part is mounted on the main chamber of the CMS machine by means of a union 10 adjustable in distance and inclination to allow optimum positioning of the spot of $Cs^0$ on the useful zone. The axis of the evaporator forms an angle of 45° with respect to the normal to the sample.

When the end piece of the external part guide tube is brought into contact with the entry plate of the internal part by means of the translator 9, the Cs vapour can propagate itself in a second stainless steel tube 11 which has an internal diameter of 8 mm and is 177 mm long. At the end of this tube 11 is a metal support plate on which is mounted a motorised obturation system 12 which allows the stream of $Cs^0$ to be adjusted continuously between 0 and 100%, using a disc with slit of continuously variable width 16 driven by a stepper motor 17 (see FIG. 6).

At the exit from the obturation system 12 is located the end piece 13 of the gun which serves to further reduce the diameter of the jet of $Cs^0$. This end piece is formed by stainless steel cylinder 45 mm long with an internal diameter of 5 mm which ends in a cone with an escape hole 2 mm in diameter.

All the pipes in the internal part can be heated by means of a second heating wire 14. The temperature is monitored on the end piece of the gun by means of another chromel-alumel thermocouple 15.

1.3. Characterisation 1.3.1. Thermal Behaviour

Because of their different weights and environments, i.e. vacuum for the internal part, atmosphere for the external part, the external and internal parts present fairly different thermal behaviours. It is thus necessary to apply a much greater power to the heating element of the external part than to that of the internal part when one wishes to raise the two tubes to the same temperature. On the other hand, the fact that the external part loses a considerable proportion of the heat received to the external environment via the evaporation block and via the bellows of the translation system, the surface of which is comparable to that of a radiator, allows the temperature of the reservoir to be lowered quickly with a view to stopping the evaporator.

While the internal part must be raised rapidly to a temperature of 110° C. to avoid any risk of condensation and obturation in the various tubes, the heating power brought to the external part should be increased in successive steps to guarantee progressive heating of the Cs reservoir.

1.3.2. $Cs^0$ Evaporation Rates: Calibration of Deposition Rates

In order to be able to measure the stream of neutral Cs delivered by the evaporator, a quartz microbalance system was installed on the CMS machine. The measuring device consists of a Leybold Inficon sensor equipped with a quartz crystal covered with a layer of gold and with a working frequency of 6 MHz. Using a Leybold Inficon XTM/2 deposition monitor and after a careful calibration taking into account the adhesion of the Cs film deposited on the quartz, we thus manage to determine the stream of $Cs^0$ with an accuracy of 0.01 Å/s, which is equivalent to a deposition rate of approximately $4 \cdot 10^{-3}$ monolayers per second.

The sensor is installed by means of two tubes on a translation system occupying a flange of the main chamber on the side diagonally opposite the evaporator (not shown). This assembly enables the sensor to be moved on a horizontal axis located at the same distance from the extraction optics as the sample during the analyses. Thus the sensor can be brought in front of the stream of $Cs^0$ at the point where the sample is normally positioned and can be removed to be replaced by the sample-holder for the analyses. In addition, the system set up enables a profile to be produced through the jet of $Cs^0$ by sweeping the diagonal of the beam with the sensor.

FIGS. 7 and 8 represent the calibration curves enabling the stream of Cs to be adjusted by adapting the heating power of the reservoir. Independently from the power $P_{ext}$ applied, the internal part of the evaporator is raised during all the analyses to 110° C. From these calibration curves it can be concluded that $Cs^0$ deposition rates on the sample of the desired order of 1 Å/s can be reached with reasonable heating powers and temperatures.

As curves 7 and 8 exhibit an exponential change in the deposition rate as a function of the heating power $P_{ext}$ applied to the reservoir and of the temperature of the reservoir, even greater flow rates appear possible by increasing the temperature by only a few degrees.

Finally, we should note that the heating and evaporator flow rate stabilisation phases result in a time of approximately 90 min. to reach a deposition rate of 1 Å/s after start-up of the evaporator.

1.3.3. Pressure Conditions

The reservoir temperature range (70 ° C. to 90 ° C.) required for the evaporator to output the necessary flow corresponds according to the Cs saturating pressure curve to a pressure range in the source of between $1 \cdot 10^{-4}$ mbar and $4 \cdot 10^{-4}$ mbar. This value appears to be realistic in view of the length (approximately 40 cm) and the small diameter (between 2 mm and 8 mm) of the pipe connecting the reservoir to the main chamber through which the pumping is carried out.

In addition, we observe that the pressure in the analysis chamber remains at a quite acceptable level during the operation of the evaporator ($4 \cdot 10^{-8}$ mbar to $1 \cdot 10^{-7}$ mbar for deposition rates between 0.3 Å/s and 3.5 Å/s).

1.3.4. Stability of Deposition Rates

By recording the deposition rates indicated by the microbalance controller for various heating powers and therefore for different values of the evaporator flow rate (see example in FIG. 9 for $P_{ex}$=85 W), we determined a deposition rate stability $\Delta v_D/v_D$=2% over 60 min.

1.3.5. Dimensions of $Cs^0$ Beam

To evaluate the diameter of the spot of $Cs^0$ on the sample, we measured the deposition rate with the quartz balance for various heating powers, while moving the quartz balance on its horizontal axis using the translation system (see example in FIG. 10).

A first method for judging the diameter of the spot of $Cs^0$ produced consists in approximating the profile of the beam with a Gaussian. In this case, we obtain an average curve width of 7.5 mm. By choosing the width at mid-height as a criterion, the diameter of the spot can be evaluated at 8.7 mm. Finally, the average width at the base of the profile ($v_D$=0) is 18.5 mm.

Given the dimensions of the sample holder (10 cm×7.5 cm), we can conclude that the whole stream of $Cs^0$ delivered by the evaporator remains confined on this plate and that there is consequently no reason to fear contamination of the analysis chamber.

In addition, the beam profiles formed made it possible to verify that the maximum $Cs^0$ intensity lies directly below the extraction nose of the secondary optics, which means that the spot is correctly centred on the zone to be analysed.

1.3.6. Purity of $Cs^0$ Deposit

The cleanliness of the Cs deposit is a crucial point for the use of the $Cs^0$ evaporator during the analyses. A contamination of the Cs vapour with impurities would lead to an increase in the detection limits for certain elements given that the signal of the element in question would be affected by a background noise of varying degrees of intensity.

An elementary analysis of the layer of Cs deposited was carried out by two different means. First, samples of Si and AsGa exposed to the stream of $Cs^0$ were bombarded with $Ga^+$ ions and it was thus possible to record mass spectra in situ. Secondly, at the end of these experiments, the sample of Si used was taken out of the CMS machine to be studied on the Leica 430i Scanning Electron Microscope (LEO), given that the difference in mass between Cs (133 a.m.u.) and Si (28 a.m.u.) ought to guarantee a good contrast in electronic imaging. An EDX spectrum was notably produced in this second analysis.

The spectra obtained in SIMS analysis and in SEM analysis were compared with spectra of the same type produced beforehand on the untouched Si and AsGa samples. This comparison shows that the mass spectra produced while the evaporator was depositing Cs on the surface are composed of the same peaks as the spectra of the untouched samples plus the typical peaks ($Cs^+$, $Cs_2^+$, $GaCs^+$ together with $SiCs^+$ or $AsCs^+$) due to the presence of Cs atoms on the samples of Si or AsGa. However, there is no explicit trace of any contaminant. We observe for example in this context that the peaks of the alkaline elements Na and K which might feature among the impurities contained in the Cs bulb do not come out at significantly higher intensities.

As regards the EDX spectra, we can note that the spectrum recorded after the deposition comprises a fairly clear peak of O. This could be explained by the fact that the Cs deposited on the sample reacted with the ambient air during the transfer of the sample between the CMS instrument and the SEM to form Cs oxides.

In the light of these results, we can conclude that the Cs deposition at typical rates around 1 Å/s does not lead to any detectable major contamination which might hinder the analyses carried out under standard $Ga^+$ bombardment conditions.

2. Experimental Procedure

2.1. Principle

2.1.1. Characteristic Parameter $\tau$

The Cs concentration is adjusted by means of the ratio between the current delivered by the analysis beam, which was for test purposes a beam of $Ga^+$ ions, and the quantity of Cs deposited by the evaporator.

To characterise the analysis conditions, we define the parameter $\tau$ expressing the ratio between the stream of $Cs^0$ and the $Ga^+$ current by means of the deposition rate $v_D$ and the erosion rate $v_{er}$:

$$\tau = \frac{v_{er}}{v_D} \quad (1)$$

Qualitatively, we can therefore now assert that the Cs concentration ($c_{Cs}$) and the parameter $\tau$ vary in opposite directions. The greater $\tau$ becomes, the more the quantity of sputtered matter increases and the lower the proportion of Cs becomes.

2.1.2. Cs Concentration Produced

Let us consider a sample of density $\rho_M$. If we designate by Y the sputtering yield characterising the primary bombardment conditions for the type of sample considered and by $\rho_{Cs}$ the atomic density of the layer of Cs formed, the Cs concentration can be written:

$$c_{Cs} = \frac{1}{1 + (\tau - 1) \cdot \frac{\rho_M}{\rho_{Cs}} + \frac{\tau}{Y}} \quad (2)$$

It is important to note that, according to the relationship above, the Cs concentration depends on the characteristics of the sample analysed—by way of its density $\rho_M$ and its characteristic sputtering yield Y for the given bombardment conditions—together with the ratio $\tau$ between the $Cs^0$ erosion and deposition rates, but not the values in themselves of these two rates.

2.2. Experimental Study
2.2.1. Experimental Conditions

To practically test the method of analysis consisting of a $Ga^+$ bombardment accompanied by a deposition of $Cs^0$, we used samples of aluminium, silicon and nickel, given that these materials cover a considerable range on the work function scale.

The reservoir of the $Cs^0$ evaporator was heated with varying powers in order to obtain different values of the deposition rate $v_D$.

The $Ga^+$ gun was operated at an energy of 28 keV and the sample polarised at +4500 V was positioned at a distance d=2.5 mm from the extraction nose. These conditions result in an angle of incidence of the primary ions of è=54° with an impact energy of E=23.5 keV.

In order to be able to vary the parameter ô while at the same time keeping the deposition rate constant, we changed the density of bombardment with $Ga^+$ ions by adapting the dimensions of the scanning surface.

A summary of the corresponding experimental conditions are given in Table 1.

TABLE 1

| Sample holder | |
|---|---|
| Distance | d = 2.5 mm |
| Sample voltage | U = +4500 V |
| $Ga^+$ gun | |
| Primary energy | E' = 28 keV |
| Primary current | 4.0 nA < $I_p$ < 4.2 nA |
| Scanning surface | 38 × 38 μm² to 190 × 190 μm² |
| $Cs^0$ evaporator | |
| Internal heating power | $P_{int}$ = 12 W |
| Temperature of internal part | $T_{int}$ = 110° C. |
| External heating power | 80 W < $P_{ext}$ < 105 W |
| Temperature of external part | 75° C. < $T_{int}$ < 87° C. |
| Deposition rate | 0.9 Å/s < $v_D$ < 3.5 Å |

2.2.2. Accessible Cs Concentration Range

FIG. 11 shows, in an example, the change in the Cs concentration determined experimentally—knowing the quantity of Cs deposited, the number of $Ga^+$ ions incorporated in the volume analysed and the volume sputtered—over the given erosion rate range for four different $Cs^0$ deposition rates for the aluminium sample.

To enable a comparison between these experimental values of $c_{Cs}$ and the theoretical evolution established in the relationship, we calculated for each measurement point the ratio $\tau$ between the erosion rate and the deposition rate and plotted all the points thus obtained on the same graph.

The experimental curve of the aluminium sample resulting from this transformation operation is plotted together with the respective theoretical behaviour of $c_{Cs}$ as a function of the parameter $\tau$ in FIG. 12.

Several conclusions can be drawn from FIG. 12. First of all, the result supplied by the theoretical relationship, namely that the value of $c_{Cs}$ depends only on the ratio between the erosion and deposition rates and not on the individual values, was corroborated experimentally. The four curves obtained for each sample when converting the erosion rate scale into a parameter $\tau$ scale are almost perfectly superimposed.

Secondly, the graphs show a very good agreement between the experimental results and the theoretical forecasts for values of $\tau$ greater than about 6. For lower values, the gap between the two curves becomes increasingly wider, while their general appearance (shape of the curve) remains generally the same. We find the same limitations concerning the area of validity of the theoretical equation (2) encountered at the time of establishment of this relationship: the theoretical forecasts are correct provided that the Cs concentration is not too great, i.e. $\tau$ does not become too small.

2.2.3. Study of Useful Yields Attained

A systematic study clearly revealed that the useful yield—which expresses the sensitivity of the analysis—of the $Cs_x^+$ and $MCs_x^+$ clusters detected by sputtering the sample with an ion beam while simultaneously depositing neutral Cs depends solely on the ratio $\tau$ between the erosion rate and the deposition rate, but not on the values of these two rates as such (see the example in FIG. 13). we were therefore able to verify experimentally the following transitivity rule: given that the useful yield is a function of the Cs concentration, and as this latter value depends on the parameter $\tau$, the useful yield of the $Cs_x^+$ and $MCs_x^+$ clusters is a function of $\tau$.

2.3. Comparison Between the Performances of the CMS Instrument and Those of the Cameca IMS 4f and IMS LAM It is interesting to summarise in the same comparative table the maximum values of the useful yields determined above for the method of sputtering by an ion beam using a simultaneous deposit of $Cs^0$ and those attained for the same three samples on the Cameca IMS 4f and Cameca IMS LAM instruments operated under standard conditions, namely an extraction voltage of +4500 V and a primary energy of 10 keV (Table 2).

These three instruments use the same secondary optics and measurements have shown that the transmission of these secondary optics are identical.

TABLE 2

| Sample | Signal | CMS $Cs^0$ | IMS 4f/IMS LAM |
|---|---|---|---|
| Al (Φ = 4.28 eV) | $Cs^+$ | 3.6 · 10⁻¹ | 3.8 · 10⁻³ |
| | $AlCs^+$ | 1.3 · 10⁻⁴ | 5.4 · 10⁻⁶ |
| Si (Φ = 4.85 eV) | $Cs^+$ | 3.6 · 10⁻¹ | 6.5 · 10⁻² |
| | $SiCs^+$ | 1.6 · 10⁻⁵ | 1.1 · 10⁻⁵ |
| Ni (Φ = 5.15 eV) | $Cs^+$ | 3.6 · 10⁻¹ | 3.1 · 10⁻¹ |
| | $NiCs^+$ | 8.5 · 10⁻⁵ | 2.0 · 10⁻⁴ |

It can be seen that the useful yields determined using a deposit of $Cs^0$ are higher (for materials with a low work function) and only slightly lower (for materials with a high work function) than the corresponding values obtained on conventional Cameca instruments. These differences can be explained by considering factors such as the work function variations induced by the Cs deposit, the reductions resulting from the probability of ionisation of the Cs, the cluster formation processes, the spatial and temporal correlation of the partners involved, etc.

Considering this comparison concerning the useful yields obtained together with the successful separation of the Cs sputtering and implantation stages during the analyses in $MCs_x^+$ mode, the potential of the $Cs^0$ deposit is undeniable.

2.4. Automation

Continuous recording of the secondary signals makes it possible to check at any moment that the analysis conditions are optimised, and if necessary, for example on passage from one layer to another, to adapt the stream of neutral Cs via the obturation system. The principle of this continuous and automatic optimisation is as follows.

By comparing the values of the various intensities at the moments t and t+dt, we define the value of ΔI as follows:

$$\Delta I \text{ comparator: } \Delta I = \begin{Bmatrix} 0 \\ 1 \end{Bmatrix} \text{ if } \begin{Bmatrix} I(t+dt) < I(t) \\ I(t+dt) > I(t) \end{Bmatrix}.$$

In addition, it is possible to define the opening (OPEN) of the obturator together with its variation (ΔOPEN). The value of C ("comparator") is then given by carrying out the logical operation C=ΔOPEN ⊙ ΔI, taking the initial condition ΔOPEN=0. Table 3 shows the corresponding logic table.

TABLE 3

| Δ OPEN | ΔI | C |
|---|---|---|
| 0 | 0 | 1 |
| 0 | 1 | 0 |
| 1 | 0 | 0 |
| 1 | 1 | 1 |

The automation programme procedure is eventually as follows:

Δ OPEN = 0
loop: calculate Δ*I*
  *C* = Δ OPEN ⊙ Δ*I*
  Δ OPEN = *C*

The electronics of the obturator is directly coupled to the automation system and reacts to its orders: if ΔOPEN=1, the opening of the shutter is increased; if ΔOPEN=0, the opening is decreased.

2.5. Conclusions

We have shown that the analysis technique consisting of a primary bombardment with $Ga^+$ ions accompanied by a simultaneous deposit of $Cs^0$ does indeed allow the Cs concentration to be varied continuously over the whole range. The value of this range depends only on the characteristics of the material analysed and the relationship between the erosion and deposition rates, but not on the individual values of these two rates.

Our experiments have proved that it is possible to carry out analyses in $MCs_x^+$ mode by sputtering the sample with a $Ga^+$ ion beam while simultaneously depositing neutral Cs with very promising useful yields. We have highlighted the fact that the behaviour of the $Cs_x^+$ and $MCs_x^+$ signals detected depends solely on the ratio τ between the erosion rate and the deposition rate, and not on the values in themselves of these two speeds.

This becomes very important within the perspective of a low-energy primary bombardment with a view to an improvement of the depth resolution: in this case the sputtering yield and consequently the erosion rate take very low values; by then lowering the deposition rate to attain optimum values of the parameter τ, we succeed in optimising the secondary signals in which we are interested.

3. EXEMPLES OF APPLICATION

In this section, we shall present a few examples of applications of this analysis technique. For these purposes, we shall make a distinction between the two main types of application of the SIMS technique, namely the depth profiles and ion imaging.

3.1. Depth Profiles

3.1.1. Implant of Mg and In in Si

The sample considered consists of a silicon substrate in which magnesium and indium ions have been implanted at an energy of 300 kev and at a dose of $10^{15}$ atoms/cm².

As the elements involved come out well in the form of $MCs^+$ clusters, a depth profile of this sample was made by recording the $MgCs^+$, $InCs^+$ and $SiCs^+$ signals. In addition, the $Cs^+$ and $Ga^+$ secondary intensities were measured in order to get an indication of the stability of the experimental conditions. Table 4 shows a summary of the corresponding experimental conditions

TABLE 4

| $Ga^+$ gun | |
|---|---|
| Primary energy | E' = 28 keV |
| Primary current | $I_p$ = 4.2 nA |
| Scanning surface | S = 70 × 70 μm² |
| $Cs^0$ evaporator | |
| Internal heating power | $P_{int}$ = 12 W |
| Temperature of internal part | $T_{int}$ = 110° C. |
| External heating power | $P_{ext}$ = 90 W |
| Temperature of external part | $T_{int}$ = 80° C. |
| Deposition rate | $v_D$ = 1.5 Å/s |
| Secondary optics | |
| Sample-extraction distance | d = 2.5 mm |
| Sample voltage | U = +4500 V |
| Diameter of zone analysed | ψ = 42 μm |
| Mass resolution | M/ΔM = 300 |
| Energy bandwidth | ΔE = 130 eV |

In accordance with the results established in the course of our study, we chose a primary bombardment density and a $Cs^0$ deposition rate such that the parameter τ is close to the optimum value (τ=4.5) for the formation of the $MCs^+$ clusters from a Si matrix. Indeed, the chosen experimental conditions lead to an erosion rate of 6.5 Å/s, and we therefore arrive at a value τ=4.3. In practice, this value of τ is adjusted by varying the dimensions of the primary raster for a given primary current intensity and a given deposition rate, in order to position oneself at the critical threshold common to the $Cs^+$ and $MCs^+$ secondary intensities.

FIG. 14 shows that our analysis technique makes it possible to obtain very good quality implantation profiles. Because of their lower mass at the same implantation energy, the Mg ions penetrated more deeply into the sample. It should also be noted that the matrix signals linked to the primary elements remain perfectly stable during the analysis.

3.1.2. Implant of Ti and Cu in Al

The second example consists of a sample of aluminium in which titanium and copper ions were implanted at an energy of 180 keV and at a dose of $10^{16}$ atoms/cm$^2$.

Once again, all the interesting elements can be detected in the form of MCs$^+$ clusters and therefore the TiCs$^+$, CuCs$^+$ and AlCs$^+$ signals were measured together with Cs$^+$ and Ga$^+$ as a function of time.

As a result of its low work function, the aluminium matrix reacts much more critically to the Cs deposit than is the case for Si. Consequently, and in accordance with the results established during our experimental study of the formation of the MCs$_x^+$ clusters, we set the parameter τ to a higher value.

By adapting the dimensions of the primary raster to position ourselves at the critical threshold common to the Cs$^+$ and MCs$^+$ secondary intensities, we arrive at a value of τ=5.6, which is in full agreement with the value determined as being optimal (τ=5.9) for the analysis of the MCs$^+$ clusters from an Al matrix. Table 5 shows a summary of the experimental conditions.

TABLE 5

| Ga$^+$ gun | |
|---|---|
| Primary energy | E' = 28 keV |
| Primary current | I$_p$ = 4.2 nA |
| Scanning surface | S = 65 × 65 ìm$^2$ |
| Cs$^0$ evaporator | |
| Internal heating power | P$_{int}$ = 12 W |
| Temperature of internal part | T$_{int}$ = 110° C. |
| External heating power | P$_{ext}$ = 90 W |
| Temperature of external part | T$_{int}$ = 80° C. |
| Deposition rate | v$_D$ = 1.5 Å/s |
| Secondary optics | |
| Sample-extraction distance | d = 2.5 mm |
| Sample voltage | U = +4500 V |
| Diameter of zone analysed | Ψ = 42 ìm |
| Mass resolution | M/ΔM = 300 |
| Energy bandwidth | ΔE = 130 eV |

3.1.3. Implant of F and Al in InP

While we exclusively measured MCs$^+$ type signals in the two first depth profiles, we chose for this third example a sample of InP in which we implanted both an electropositive element, in this case Al, which is analysed in the form of MCs$^+$ clusters and an electronegative element, namely F, which is best detected in the form of MCs$_2^+$ clusters. The Al implantation energy was 180 keV while that of the F was reduced to 130 keV because of its lower atomic mass. The implanted doses were set at $10^{16}$ atoms/cm$^2$ for the two elements.

For this depth profile, it is therefore required to record MCs$^+$ and MCs$_2^+$ type ions together with the Cs$^+$, Cs$_2^+$ and Ga$^+$ secondary signals which serve as indicators of the stability of the analysis conditions. Taking into account that the optimum values of τ depend on the particular type of secondary ion considered (Cs$^+$, Cs$_2^+$, MCs$^+$, MCs$_2^+$), we cannot simultaneously optimise all the signals and we are therefore obliged to compromise concerning the setting of the parameter τ. After experimentally determining the optimum τ values for the MCs$^+$ ions (AlCs$^+$, InCs$^+$, PCs$^+$) and for the FCs$_2^+$ clusters by way of variations of the dimensions of the primary raster, we set the final value of τ for our analysis at an intermediate value (τ=7.5) leading to major secondary intensities for all the signals under interest. Table 6 shows a summary of the corresponding experimental conditions.

TABLE 6

| Ga$^+$ gun | |
|---|---|
| Primary energy | E' = 28 keV |
| Primary current | I$_p$ = 4.2 nA |
| Scanning surface | S = 112 × 112 μm$^2$ |
| Cs$^0$ evaporator | |
| Internal heating power | P$_{int}$ = 12 W |
| Temperature of internal part | T$_{int}$ = 110° C. |
| External heating power | P$_{ext}$ = 90 W |
| Temperature of external part | T$_{int}$ = 80° C. |
| Deposition rate | v$_D$ = 1.5 Å/s |
| Secondary optics | |
| Sample-extraction distance | d = 2.5 mm |
| Sample voltage | U = +4500 V |
| Diameter of zone analysed | Ψ = 23 m |
| Mass resolution | M/ΔM = 300 |
| Energy bandwidth | ΔE = 130 eV |

We observe in FIG. 16 that all the matrix signals (PCs$^+$ and InCs$^+$) together with those linked to the primary elements (Cs$^+$, Cs$_2^+$ and Ga$^+$) take approximately 90 seconds to stabilise. This initial instability should indicate the existence of a quite considerable transient state for this type of material, which is sputtered very easily.

Concerning the two elements implanted, we observe again that the implantation profiles recorded are of very good quality.

3.2. Ion Imaging

To demonstrate the possibility of producing ion images in MCs$_x^+$ mode by scanning the surface of the sample with a fine Ga$^+$ ion beam while simultaneous depositing Cs$^0$ atoms on it, we recorded images of a grid by successively detecting four different elements (FIG. 17).

The chosen grid consists of a substrate of aluminium incorporating copper bars 5 μm wide at 20 μm intervals.

Given that the enlargement of the ion image directly depends on the dimensions of the primary sweep and that strong secondary intensities are not required, the parameter τ is not optimised in this example. Table 7 shows a summary of the corresponding experimental conditions

TABLE 7

| Ga$^+$ gun | |
|---|---|
| Primary energy | E' = 28 keV |
| Primary current | I$_p$ = 600 pA |
| Scanning surface | S = 38 × 38 μm$^2$ |
| Cs$^0$ evaporator | |
| Internal heating power | P$_{int}$ = 12 W |
| Temperature of internal part | T$_{int}$ = 110° C. |
| External heating power | P$_{ext}$ = 75 W |
| Temperature of external part | T$_{int}$ = 75° C. |
| Deposition rate | v$_D$ = 0.6 Å/s |
| Secondary optics | |
| Sample-extraction distance | d = 2.5 mm |
| Sample voltage | U = +4500 V |
| Mass resolution | M/ΔM = 300 |
| Energy bandwidth | ΔE ≈ 5 eV |

By detecting the CuCs$^+$ and AlCs$^+$ secondary ions, we manage to display only the bars forming the grid and the areas bounded by these bars. However, if we record the Cs$^+$ or $Cs_2^+$ signals, we obtain a contrast image in which the areas between the bars appear to be raised.

The invention claimed is:

1. Method for modifying electronic properties of a sample surface to analytical ends, comprising in situ deposition of neutral cesium ($Cs^0$), under ultra-high vacuum, said neutral cesium being enabled in the form of a collimated adjustable stream, said $Cs^0$ deposition being simultaneously accompanied by a primary bombardment of said surface, in the form of at least a beam comprising electrons and/or ions or neutral atoms or groups of atoms, or by an X-ray irradiation, intended to induce a secondary emission or sputtering of particles for analysis, out of the surface, said sputtering comprising secondary electrons and/or $Cs_x^{n+}$ and/or $MCs_x^{n+}$ positive clusters (x=1, 2) and/or $M^{m-}$ negative ions and/or $M^{m+}$ positive ions, M being a constituent of the sample material made of an atom or a group of atoms (n, m integers), the $Cs^0$ deposition being decoupled from the primary bombardment conditions, to provide a simultaneous optimization of deposited $Cs^0$ concentration and analytical characteristics, such as the depth resolution, characterized in that said optimized deposited $Cs^0$ concentration is chosen only by adjusting the ratio ($\tau=V_{er}/V_D$) between the erosion rate ($v_{er}$) and the $Cs^0$ deposition rate ($V_D$), for a given sample and given primary bombardment conditions.

2. Method according to claim 1, wherein said optimized deposited $Cs^0$ concentration is continuously adjustable according to the relation:

$$c_{Cs} = \frac{1}{1 + (\tau - 1) \cdot \frac{\rho_M}{\rho_{Cs}} + \frac{\tau}{Y}},$$

wherein $\rho_M$ is the density of the sample constituent, $\rho_{Cs}$ the atomic density of the layer of Cs formed and Y the sputtering yield characterizing the primary bombardment conditions for the sample considered.

3. Method according to claim 1, wherein the stream of $Cs^0$ is provided and collimated in a column by means of:
a temperature adjustment of an evaporator comprising a metallic cesium reservoir, and/or
an aperture control of a motorized obturator located in the path of the cesium stream.

4. Method according to claim 3, wherein the reservoir temperature range is maintained between 70 and 90° C., corresponding to a pressure range from $1.10^{-4}$ to $4.10^{-4}$ mbar and in that the stability of the deposition rate is about 2% over 60 minutes.

5. Method according to claim 3, wherein the stream of $Cs^0$ is automatically and continuously adapted via the obturator.

6. Method according to claim 1, wherein it is coupled to static or dynamic Secondary Ion Mass Spectroscopy (SIMS), preferably operating in the $MCs_x^+$ mode (x=1, 2).

7. Method according to claim 6, wherein the deposition rate of $Cs^0$ is continuously adjustable in the range from 0 to 10 Å/s, corresponding about to 0–4 monolayers per second.

8. Method according to claim 1, wherein it is coupled to electron spectroscopy.

9. Method according to claim 8, wherein electron spectroscopy is selected from the group consisting of Auger Electron Spectroscopy (AES), Electron Energy Loss Spectroscopy (EELS), X-Ray Photoemission Spectroscopy (XPS) and Ultraviolet Photoemission Spectroscopy (UPS).

10. Method according to claim 1, wherein it further enables a stream of a chemical element other than Cs, evaporated under ultra-high vacuum, to create secondary emission for analytical purposes of $M_1M_2^{n+}$ clusters or $M_2^{m-}$ ions or $M_2^{m+}$ ions (n, m integers) or electrons, wherein $M_1$ and $M_2$ are respectively the atoms or groups of atoms constituted by the chemical element other than Cs and the atoms or groups of atoms from the sample.

11. Method according to claim 1, wherein the sole adjustable deposition rate of $Cs^0$ or a chemical element other than Cs to an optimized value enables to optimize the intensity of secondary particles emitted by the sample.

12. Method according to claim 1, wherein the useful yield, i.e. the sensitivity of the secondary emission species, preferably $M^{n-}$, $M^{m+}$, and still more preferably $Cs_x^{n+}$ and $MCs_x^{n+}$, is approximately optimized solely by adjusting said ratio ($\tau$).

13. Energy and/or mass analyzer instrument for carrying out the method according to claim 1, comprising a neutral cesium ($Cs^0$) deposition column, capable of delivering an adjustable and stable stream of pure neutral cesium, said neutral cesium column being usable simultaneously with a primary bombardment or a primary irradiation column, and comprising an evaporation block (1) including a reservoir (5) filled with pure metallic cesium, equipped with temperature control means (6,7), prolongated by a tube (2,11) up to a gun end piece (13) located close to the sample and equipped with beam collimation means (12), characterized in that said tube (2, 11) and gun end piece (13) equipped with beam collimation means (12) are further equipped with temperature control means (8,14,15) for preventing condensation and obturation risks.

14. Instrument according to claim 13, wherein the evaporation block (1) is located in an external part which can be isolated from the main chamber (3) of the instrument by means of a gate valve (4) and capable of being separately pumped and vented.

15. Instrument according to claim 13, wherein said beam collimation means comprise a motorized continuously adjustable obturator (12), preferably comprising a rotary disk using a slit of continuously variable width (16), said disk being driven by a stepper motor (17).

16. Instrument according to claim 13, wherein, at the operation temperature, the neutral cesium ($Cs^0$) is in liquid state and the evaporation block (1) lies with an inclination angle such as said liquid remains in the bottom of the reservoir (5) under gravity effect.

17. Instrument according to claim 13, preferably a static or dynamic secondary ion mass spectrometry (SIMS) instrument, comprising a primary bombardment column and a secondary column equipped with secondary ion extraction means, a mass spectrometer, preferably of the type TOF (Time-Of-Flight), quadrupolar or with magnetic sector and ion detection means.

* * * * *